(12) United States Patent
Joshi et al.

(10) Patent No.: US 9,024,043 B2
(45) Date of Patent: May 5, 2015

(54) PIMARANE DITERPENES FROM ANISOCHILUS VERTICILLATUS

(75) Inventors: Swati Pramod Joshi, Maharashtra (IN); Roshan Rajan Kulkarni, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/236,995

(22) PCT Filed: Aug. 6, 2012

(86) PCT No.: PCT/IN2012/000544
§ 371 (c)(1),
(2), (4) Date: Feb. 4, 2014

(87) PCT Pub. No.: WO2013/021399
PCT Pub. Date: Feb. 14, 2013

(65) Prior Publication Data
US 2014/0171662 A1    Jun. 19, 2014

(30) Foreign Application Priority Data

Aug. 5, 2011 (IN) .......................... 2226/DEL/2011

(51) Int. Cl.
    *C07D 493/08* (2006.01)
    *C07C 35/42* (2006.01)
    *C07C 13/60* (2006.01)
    *C07C 409/18* (2006.01)
    *C07D 319/14* (2006.01)

(52) U.S. Cl.
    CPC .............. *C07D 493/08* (2013.01); *C07C 35/42* (2013.01); *C07C 13/60* (2013.01); *C07C 2103/26* (2013.01); *C07C 409/18* (2013.01); *C07D 319/14* (2013.01)

(58) Field of Classification Search
    USPC ........................................... 549/358; 568/817
    See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Lekphrom et al., Bioactive Diterpenes from the Aerial Parts of *Anisochilus harmandii*, 2010, Planta Med, 76, 726-728.*

* cited by examiner

*Primary Examiner* — Kristin Vajda
(74) *Attorney, Agent, or Firm* — Abelman, Frayne & Schwab

(57) ABSTRACT

This invention discloses diterpenes class of novel compounds of general formula I from a novel source. More particularly the invention relates to extracts/fractions containing pimarane diterpenes from *Anisochillus* (Lamiaceae), useful for prevention, treatment, inhibition or controlling growth and proliferation of mycobacterial activity in mammals. The invention further relates to extracts, fractions standardized to diterpenes class of novel compounds useful for the treatment of cancers.

10 Claims, 12 Drawing Sheets

Figure 2A:
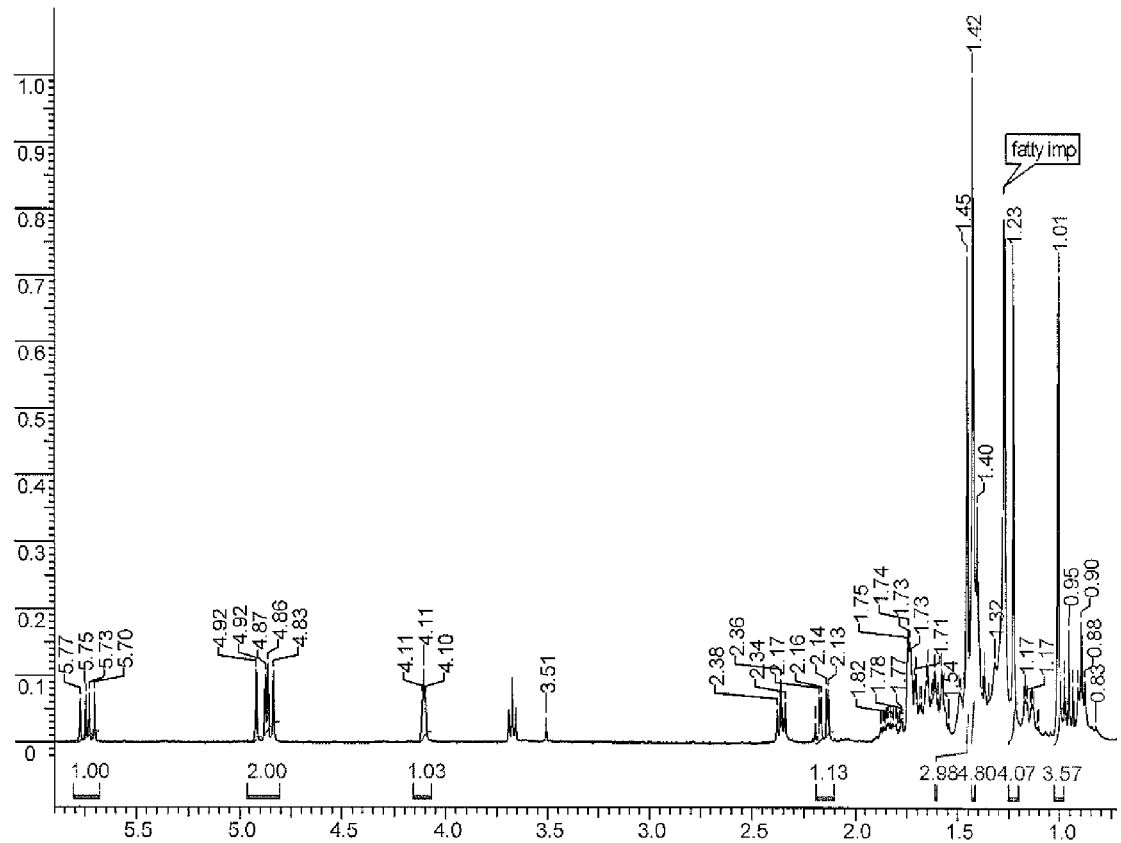

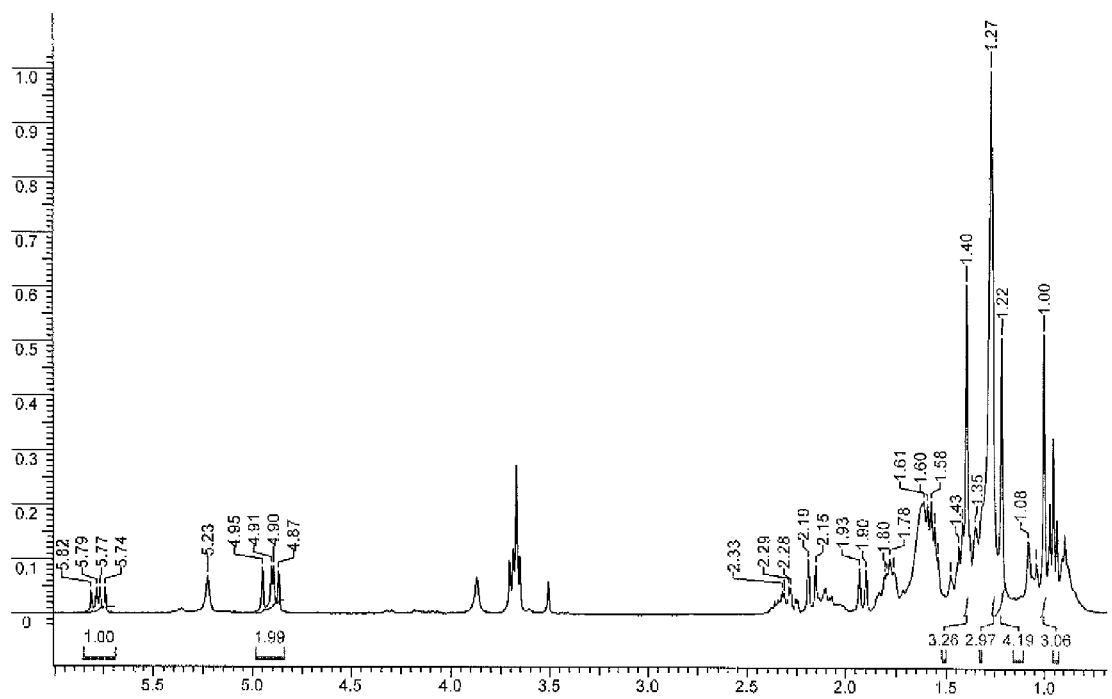
Fig. : 1a

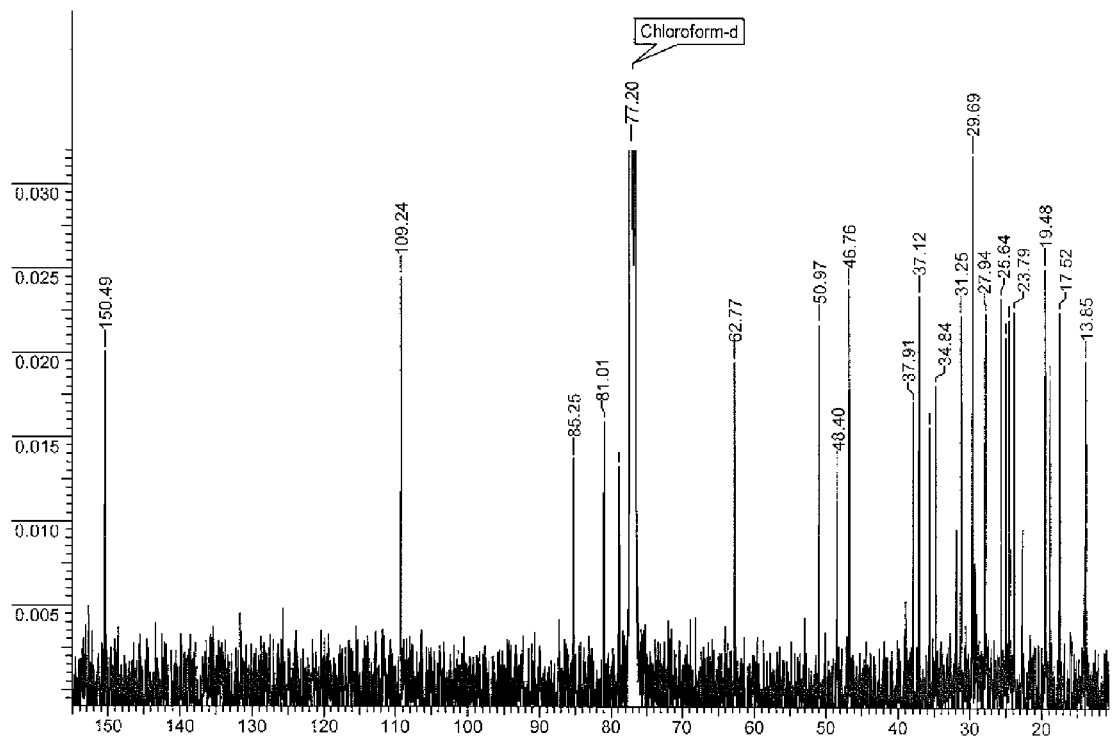
Fig. : 1b

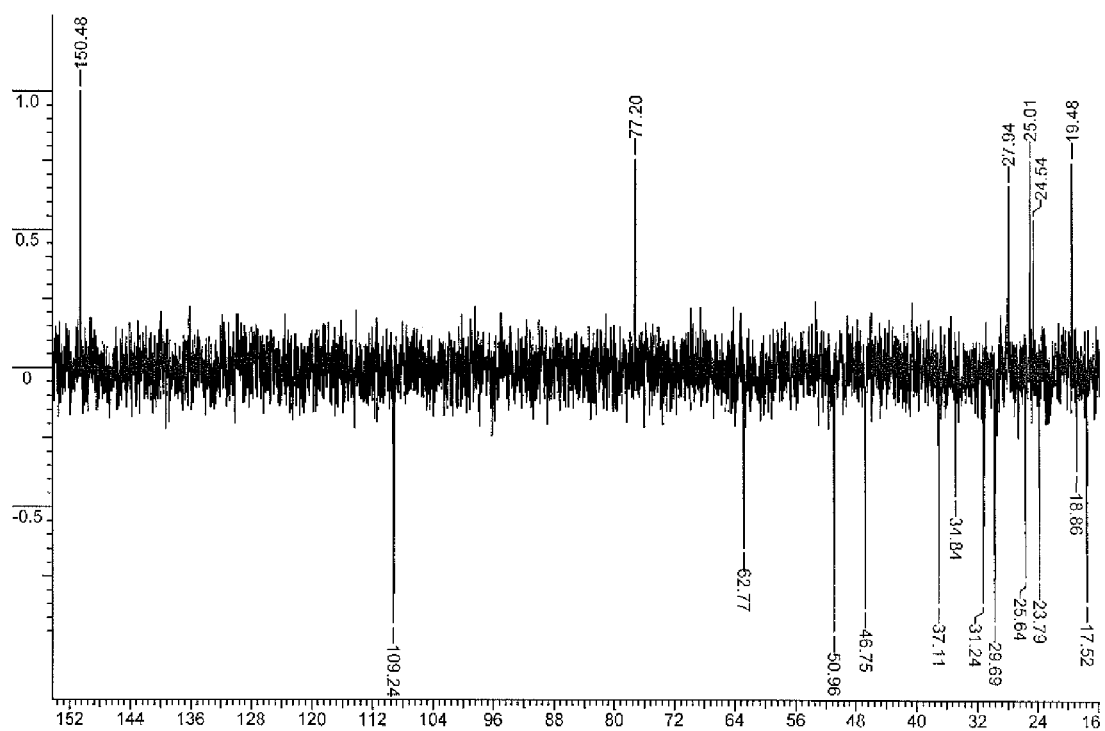
Fig. : 1c

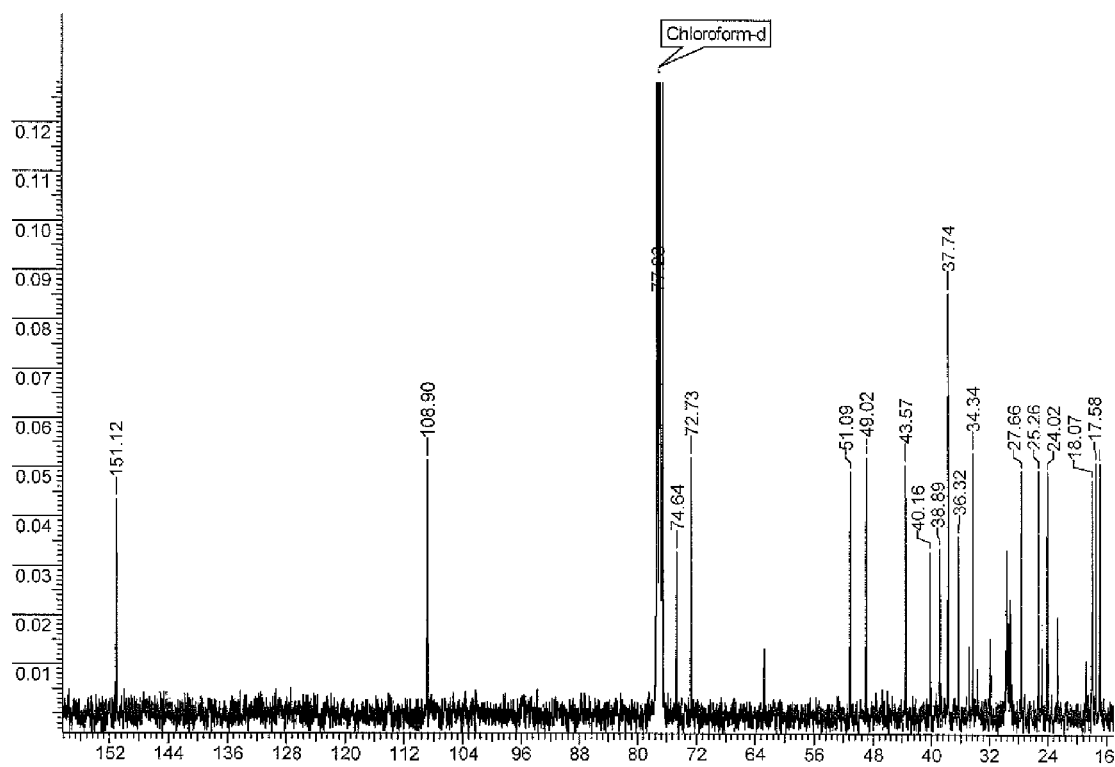
Fig.: 2b

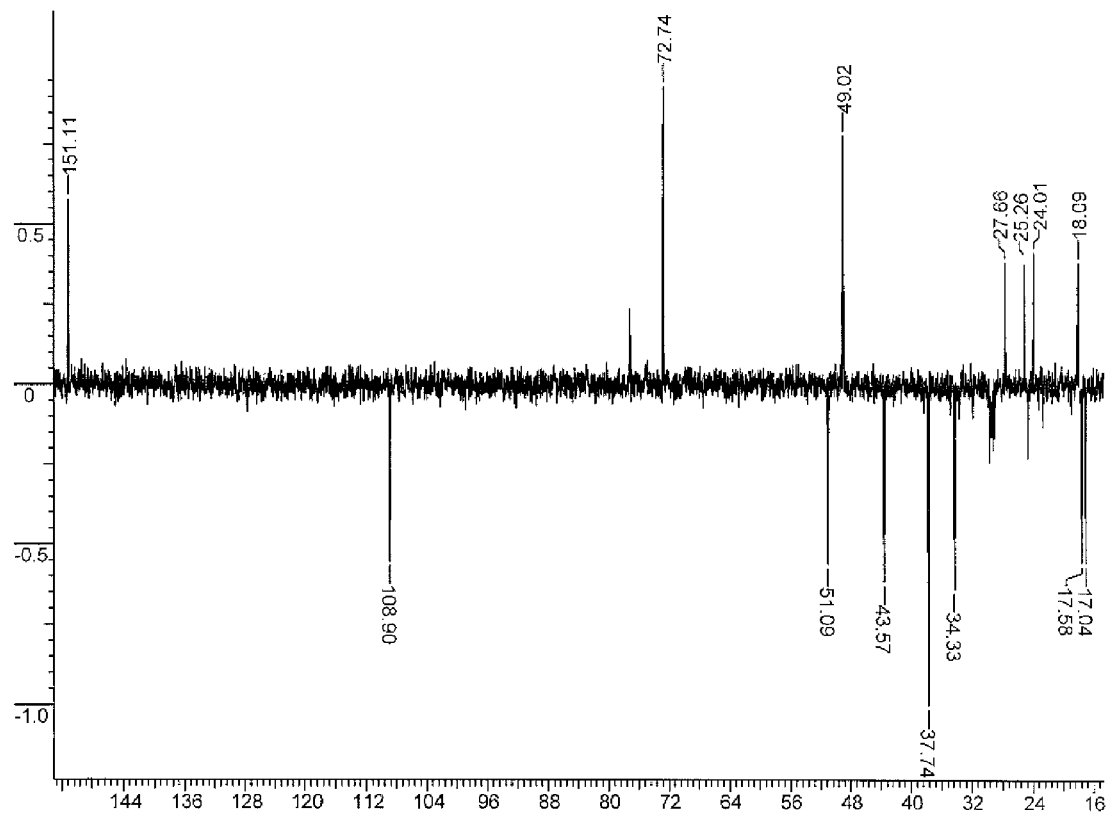
Fig.: 2c

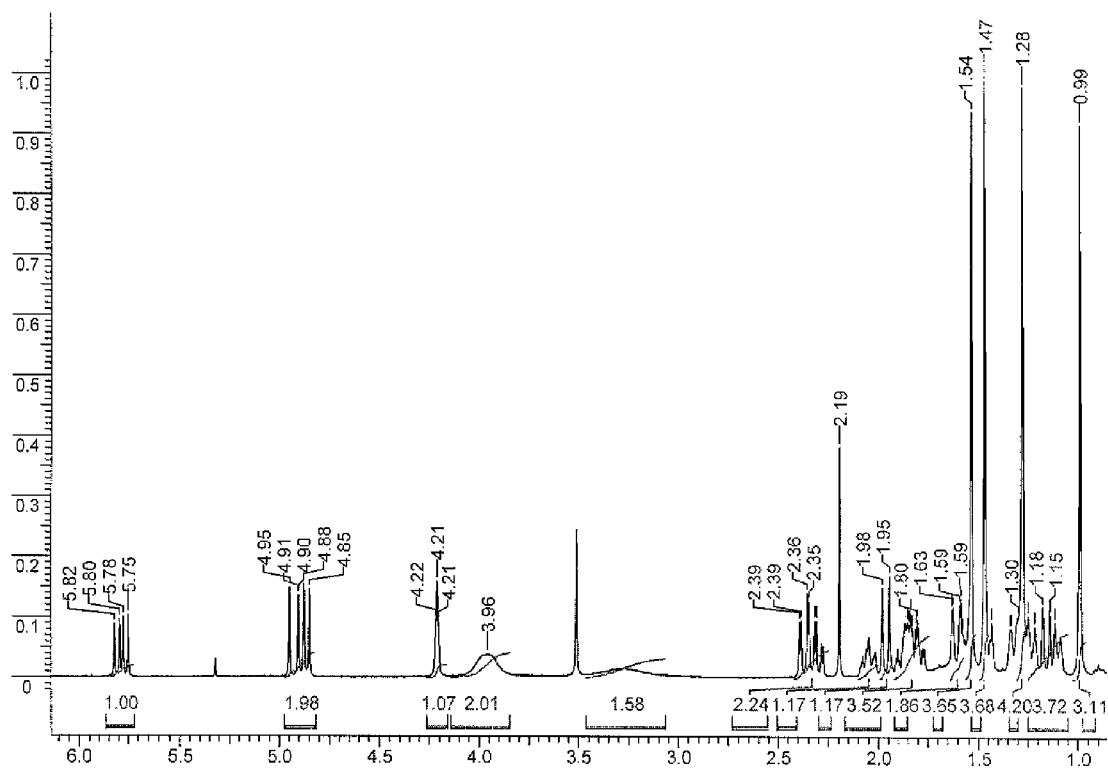
Fig.: 3a

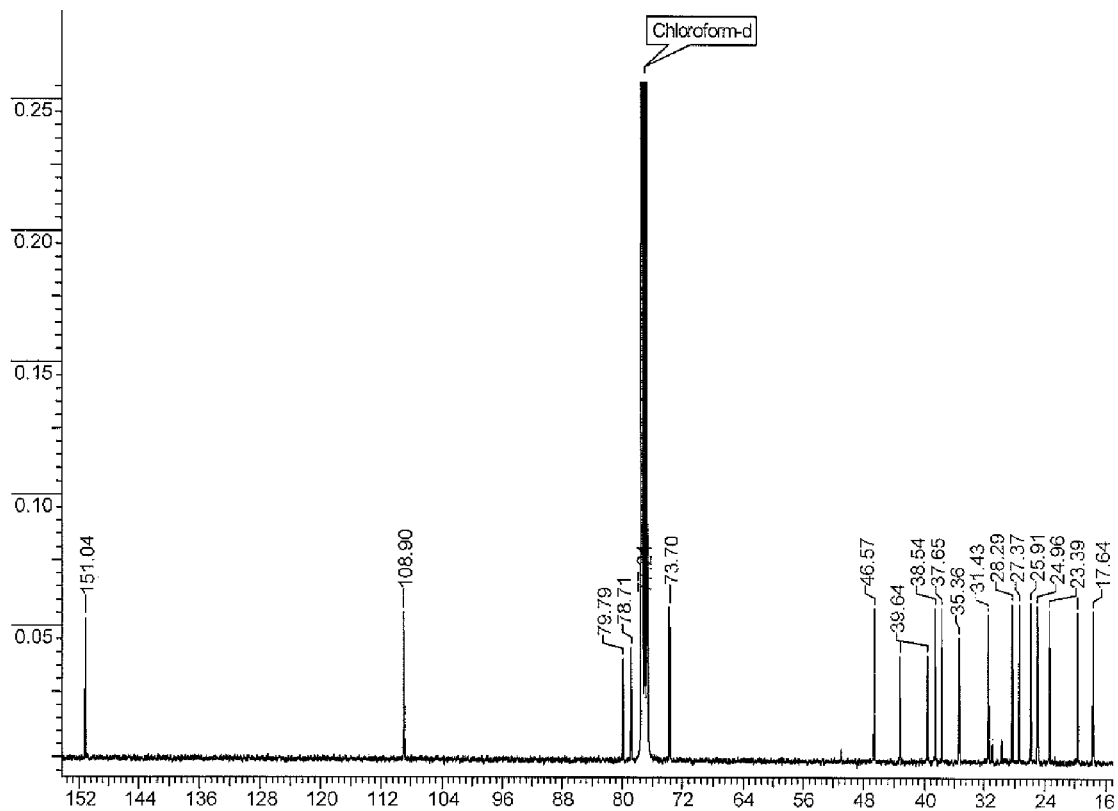
Fig.: 3b

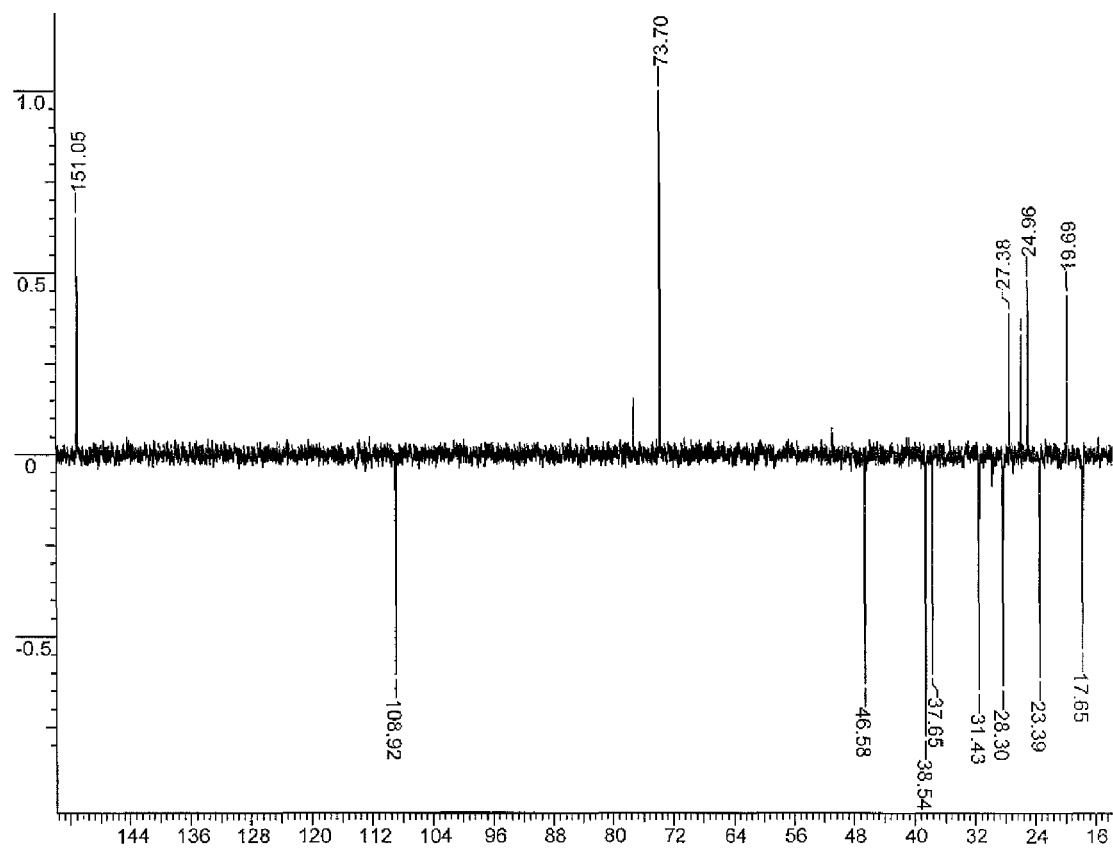
Fig.: 3c

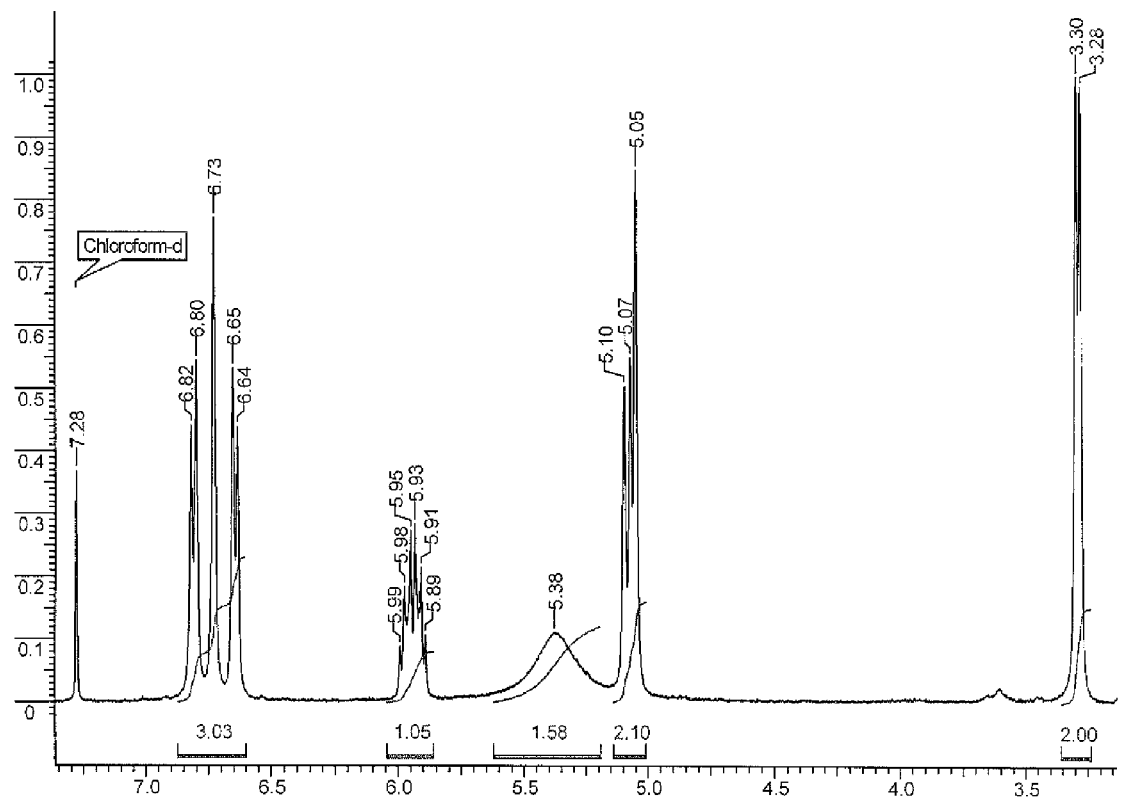
Fig.: 4a

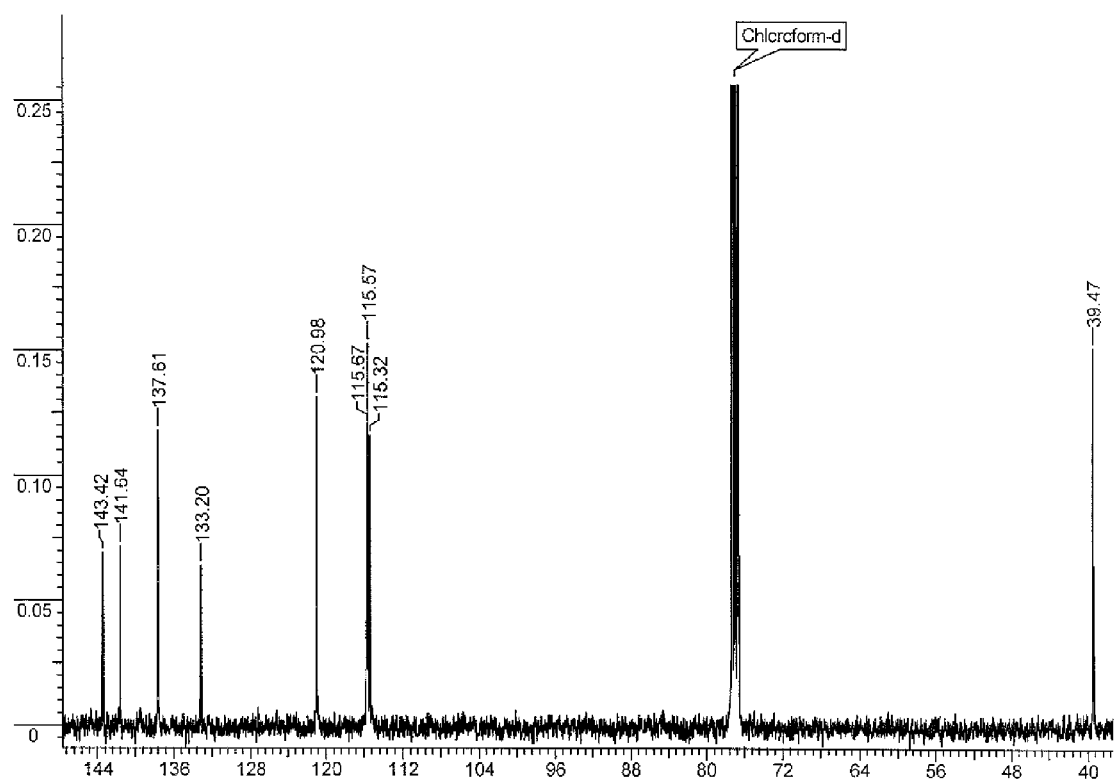
Fig.: 4b

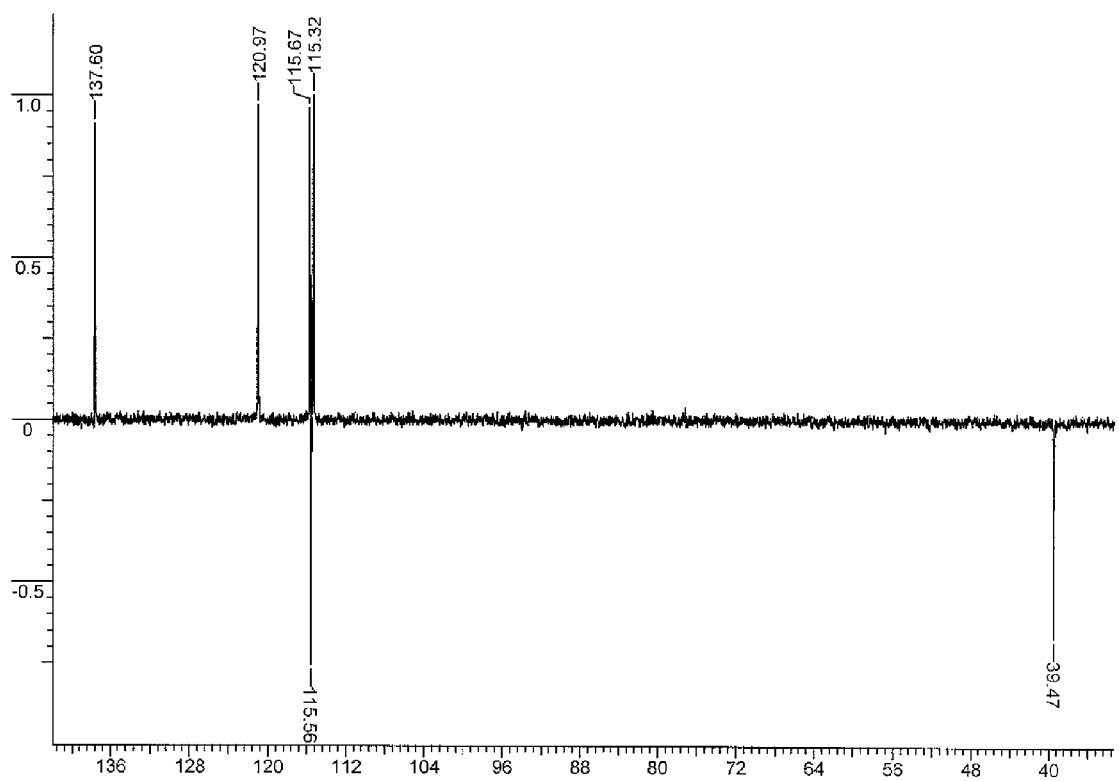
Fig.: 4c

PIMARANE DITERPENES FROM ANISOCHILUS VERTICILLATUS

CROSS-REFERENCE TO RELATED APPLICATIONS

This application is a National Phase of PCT/IN2012/000544, filed 6 Aug. 2012, which claims priority from Indian Application No. 2226/DEL/2011, filed 5 Aug. 2011, the disclosures of which are all incorporated herein by reference.

TECHNICAL FIELD OF INVENTION

This invention discloses diterpenes class of novel compounds of general formula I from a novel source. More particularly the invention relates to extracts/fractions containing pimarane diterpenes from *Anisochillus* (Lamiaceae), useful for prevention, treatment, inhibition or controlling growth and proliferation of mycobacterial activity in mammals. The invention further relates to extracts, fractions standardized to diterpenes class of novel compounds useful for the treatment of cancers.

BACKGROUND AND PRIOR ART

In the field of pharmacognosy and phytochemistry, there is an ongoing effort to find new sources for compounds that are new, or for compounds that are known to possess biological activity useful to mankind having variety of applications in diversified areas. Substantial work is undertaken to find new sources for compounds active against chronic diseases, for applications in areas such as nutrition, agriculture, well being or those affect or enhance lifestyle. With this objective the inventors have studied the isolates from *Anisochilus verticillatus*.

*Anisochilus* is an Asian genus of herbs and shrubs. The genus contains 16 species and is chiefly distributed in India, Sri Lanka, Himalaya, Burma, south China, Thailand and Indo-China with 14 species in India. Eight species are endemic to Deccan peninsula. *Anisochilus* is represented by three species in Maharashtra viz. *A. carnosus, A. verticillatus* and *A. eriocephalus*.

Little research work has been done on this genus. However, no work has been reported on two species *A. verticillatus* and *A. eriocephalus*.

U.S. Pat. No. 4,088,659 relates to pharmacological effective substance (terpenoid) of Formula-I isolated from the dried roots of plants belonging to genera *Plectranthus, Coleus, Anisochilus, Lavandula* and *Leonitis* of Labiate/Lamiacae Family, for the treatment of cardiac and circulatory diseases.

An article titled "Bioactive diterpenes from the aerial parts of *Anisochilus harmandii*" by Lekphrom R. in Planta Med. 2010 May; 76(7):726-8. discloses two new diterpenes, 4-triptobenzene L and 12-O-deacetyl-6-O-acetyl-19-acetyloxycoleon as well as eight known diterpenes which are isolated from the aerial parts of *Anisochilus hamandii* (Lamiaceae).

In accordance with the above objective, a wide range of plant extracts were screened for their inhibitory potential against the tuberculosis. The extracts of *Anisochilus verticillatus* unexpectedly showed potent anti-tubercular property among the extracts screened. Also, the extracts showed anti-cancer properties that are at par with the known anti-cancer drug, paclitaxel.

SUMMARY OF THE INVENTION

Accordingly, the present invention provides diterpenes class of novel compounds of general formula I from *Anisochillus* (Lamiaceae)

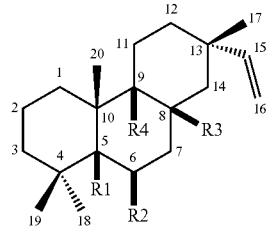

Formula I wherein R1, R, R3 and R4 could be either α or β oriented.

R1 and R3 is independently selected from the group consisting of —OH or the substituent R1 and R3 together form peroxide (—O—O—) linkage;

R2 and R4 is independently selected from the group H or OH.

In an embodiment of the present invention the compound of formula I, wherein said compound is represented by group of the following compounds

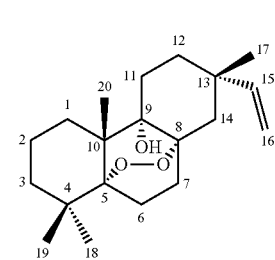

Compound 1

(2S,4aS,4bR,8aR,10aS)-2,4b,8,8-tetramethyl-2-vinyldodecahydro-8a,10a-epidioxyphenanthren-4a-ol Wherein, the substituent R1 and R3 together form peroxide (—O—O—) linkage;

R2 is hydrogen and R4 is OH; and wherein the substituents R1 to R4 are α oriented

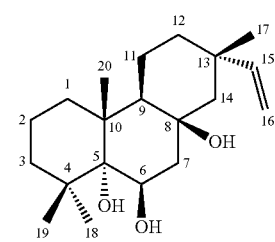

Compound 2

(2S,4aR,4bR,8aR,9R,10aS)-2,4b,8,8-tetramethyl-2-vinyltetradecahydrophenanthrene-8a,9,10a-triol Wherein, R1, R2 and R3 is independently OH and R4 is H; and wherein the substituents R1 and R2 are trans while R2 and R4 are also trans.

Compound 3

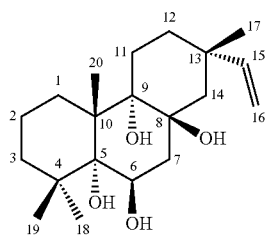

(2S,4aS,4bS,8aR,9R,10aS)-2,4b,8,8-tetramethyl-2-vinyltetradecahydrophenanthrene-4a,8a,9,10a-triol Wherein, R1, R2, R3 and R4 is independently OH; and wherein the substituents R1 and R2 are trans while R2 and R4 are also trans.

In another embodiment of the present invention Compound of formula 1, wherein said compound is isolated from *Anisochilus verticillatus*

In another embodiment of the present invention Compounds of general formula I are useful for prevention, treatment, inhibition or controlling growth and proliferation of cancer/tubercular activity in mammals.

In another embodiment of the present invention Compounds of general formula I are useful for treating or controlling proliferation of tuberculosis in a mammal.

In another embodiment of the present invention Compounds of general formula I, wherein % inhibition on Thp-1 cell line of compound 3 is 57.23 at 100 µg/ml.

In another embodiment of the present invention Compounds of general formula I, wherein $IC_{90}$ value of compounds of general formula I against *M. tuberculosis* is in the range of 12.5 to 42.92 µg/ml.

In another embodiment of the present invention a process for the extraction of Compounds of general formula I as claimed in claim 1, wherein the said process comprising the steps of
i). Pulverized aerial parts of *A. verticillatus* followed by extraction with acetone at room temperature in the range of 25 to 30° C., filtering acetone solubles and concentrating under reduced pressure in the range of 50-100 mm Hg to obtain a greenish acetone extract,
ii) separating the extract of step i) by using column chromatography (CC) with increasing polarity of the polar solvent with gradient of acetone from 5% to 50% in pet ether to obtain 18 fractions (AV1-AV18).
iii) subjecting fraction AV3 of step ii) to CC with gradient of acetonitrile from 0.5% to 3% in chloroform to collect 8 fractions (AV3a-h), iv) subjecting fraction AV4 of step ii) CC using gradient of acetonitrile from 1% to 4% in chloroform to collect 13 fractions (AV4a-m),
v) combing fractions AV4i, AV4j of step iv) and AV3h of step v) and subjected to CC with 3% acetonitrile in chloroform to obtain mixture of compounds 1 and 2 and separating and purifying by preparative TLC using 20% acetone in cyclohexane as developing system.
vi) crystallizing from fractions AV4k, AV4l and AV4m of step iv) compound 3,
vii) subjecting fraction AV5 of step ii) to CC using elution gradient acetonitrile from 1% to 15% in chloroform to collect 15 fractions (AV5a-o),
viii) subjecting fractions AV5n and AV5o of step vii) to preparative TLC using developing system 10% ethyl acetate in benzene to isolate compound 4.

In another embodiment of the present invention a pharmaceutical compositions comprising at least one compound selected from pimarane diterpenes class of compounds of general formula I for prevention, treatment, inhibition or controlling growth and proliferation of tuberculosis in mammals.

In another embodiment of the present invention a pharmaceutical compositions comprising at least one compound selected from pimarane diterpenes class of compounds of general formula I for prevention, treatment, inhibition or controlling growth and proliferation of variety of cancer in mammals.

DETAILED DESCRIPTION OF FIGURES

FIG. 1a depicts the $^1$H NMR of compound 1.
FIG. 1b depicts the $^{13}$C NMR of compound 1.
FIG. 1c depicts the DEPT NMR of compound 1.
FIG. 2a depicts the $^1$H NMR of compound 2.
FIG. 2b depicts the $^{13}$C NMR of compound 2.
FIG. 2c depicts the DEPT NMR of compound 2.
FIG. 3a depicts the $^1$H NMR of compound 3.
FIG. 3b depicts the $^{13}$C NMR of compound 3.
FIG. 3c depicts the DEPT NMR of compound 3.
FIG. 4a depicts the $^1$H NMR of compound 4.
FIG. 4b depicts the $^{13}$C NMR of compound 4.
FIG. 4c depicts the DEPT NMR of compound 4.

DETAILED DESCRIPTION OF INVENTION

The invention discloses extracts/fractions standardized to pimarane diterpenes class of compounds of general formula I isolated from *Anisochilus verticillatus* (Lamiaceae). *A. verticillatus* is an erect annual herb growing up to 1 m tall. It is endemic to India, occurring in Deccan peninsula. Entire mature plants, in flowering, were collected from Purandar Fort area, district, Pune in October, 2008. A herbarium is deposited in Botanical Survey of India, Western Circle, Pune (Accession No. SPJ-1). Plant material was cleaned off adhering dust and unwanted plant material. Roots were separated and aerial parts, dried in shade, cut and powdered in pulverizer.

The pulverized aerial parts were subjected to an extraction procedure using conventional solvents such as acetone. The extract was further subjected to series of column chromatography (CC) using conventional mobile phases such as acetone, methanol, ethyl acetate, acetonitrile, chloroform, petroleum ether or combinations thereof leading to isolation of compounds. The isolation scheme is as shown in scheme 1.

*A. verticillatus* aerial acetone 38.0 g

↓

CC 18 fractions

↓

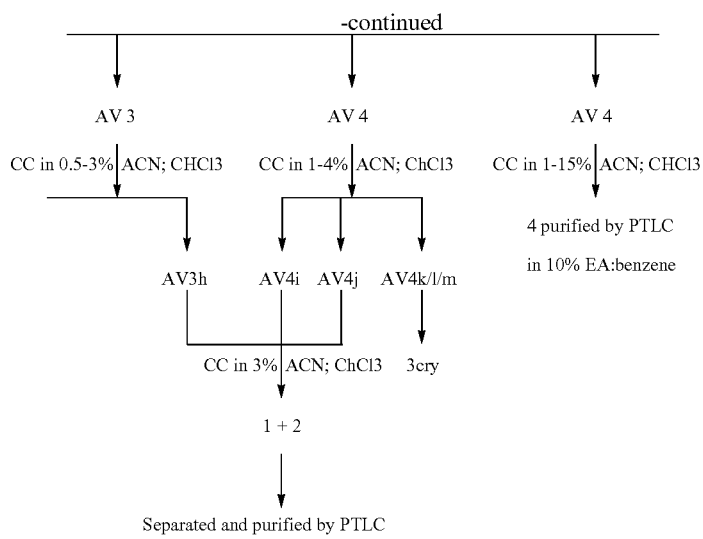

ACN: acetonitrile, CHCL3: chloroform, EA: ethyl acetate

The compounds as isolated from Scheme 1 were subjected to structural elucidation by methodologies and analytical techniques known to person skilled in the art and found to comprise pimarane diterpenes class of novel compounds of formula I encompassing formulae 1, 2 and 3 and a known compound 4 (hydroxychavicol) as shown herein, confirmed further by the NMR spectra as shown in the figures of the NMR spectra and detailed in Table 1 and Table 2. The pimarane diterpenes class of novel compounds of formula I encompassing the individual compounds of formula 1 to 3 isolated from the standardized extract/fractions according to the process of invention are as shown below:

Pulverized aerial parts (1.13 kg) were extracted with acetone (3 L×3×14 h) at room temperature. The acetone solubles were filtered and concentrated under reduced pressure to yield a greenish acetone extract which was separated by column chromatography (CC) eluting with increasing polarity of acetone from 5 to 50% in petroleum ether to collect 18 fractions (AV1-AV18).

Fraction AV3 was subjected to CC using elution gradient acetonitrile from 0.5% to 3% in chloroform to collect 8 fractions (AV3a-h).

Fraction AV4 was subjected to CC using gradient of acetonitrile from 1% to 4% in chloroform as mobile phase to collect 13 fractions (AV4a-m).

Fractions AV4i, AV4j and AV3h were combined and subjected to CC in 3% acetonitrile in chloroform to obtain mixture of compounds 1 and 2 which was separated and purified by preparative TLC using 20%, acetone in cyclohexane as developing system.

From fractions AV4k, AV4l and AV4m, compound 3 was separated by crystallisation.

Fraction AV5 was subjected to CC using elution gradient acetonitrile from 1% to 15% in chloroform to collect 15 fractions (AV5a-o). Fractions AV5n and AV5o contained compound 4, which was purified by preparative TLC using developing system 10% ethyl acetate in benzene.

General Formula I

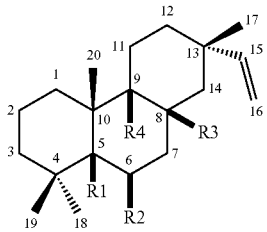

wherein R1, R, R3 and R4 could be either α or β oriented.
R1 and R3 is independently selected from the group consisting of —OH or the substituent R1 and R3 together form peroxide (—O—O—) linkage;
R2 and R4 is independently selected from the group H or OH.
The invention encompasses novel compound of formula 1.

Compound 1

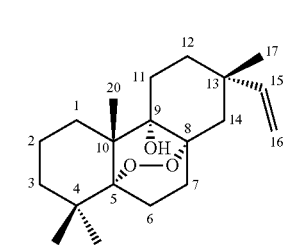

(2S,4aS,4bR,8aR,10aS)-2,4b,8,8-tetramethyl-2-vinyldodecahydro-8a,10a-epidioxyphenanthren-4a-ol Wherein, the substituent R1 and R3 together form peroxide (—O—O—) linkage;
R2 is hydrogen and R4 is OH; and wherein the substituents R1 to R4 are α oriented.
Thus the invention encompasses novel compound of formula 2.

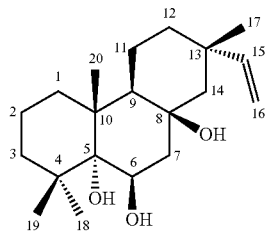

Compound 2

(2S,4aR,4bR,8aR,9R,10aS)-2,4b,8,8-tetramethyl-2-vinyltetradecahydrophenanthrene-8a,9,10a-triol Wherein, R1, R2 and R3 is independently OH and R4 is H; and wherein the substituents R1 and R2 are trans while R2 and R4 are also trans.

Thus the invention further encompasses novel compound of formula 3.

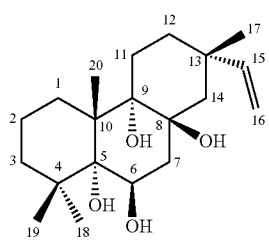

Compound 3

(2S,4aS,4bS,8aR,9R,10aS)-2,4b,8,8-tetramethyl-2-vinyltetradecahydrophenanthrene-4a,8a,9,10a-triol Wherein, R1, R2, R3 and R4 is independently OH; and wherein the substituents R1 and R2 are trans while R2 and R4 are also trans.

The compound of formula 4, a known compound is also isolated from the standardized extract isolated from *A. verticillatus* as shown below:

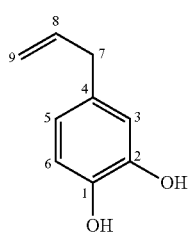

4

4-allylbenzene-1,2-diol

Thus the invention provide extract(s) or fraction(s) standardized to pimarane diterpenes class of compounds of formula I isolated from *A. verticillatus* (Lamiaceae), consisting of Compounds 1-4 viz., pimarane-5,8-peroxide, pimarane-triol, pimarane-tetrol and Hydroxychavicol respectively optionally in combination with at least one pharmaceutical carrier/excipient.

The compounds 1-4 are isolated from the fractions/extracts using at least one separation technique selected from partition(s), precipitation(s), crystallization, normal phase chromatography, reversed phase chromatography, size exclusion chromatography and ion exchange chromatography or combinations thereof.

Structures of Compounds is elucidated by detail analysis of their NMR spectra as given in FIGS. 1 to 4 and Tables 1 and 2.

TABLE 1

$^1$H and $^{13}$C NMR values for compounds 1, 2, 3 (in CDCl$_3$)

| | 3 | | 1 | | 2 | |
|---|---|---|---|---|---|---|
| no | $\delta_C^1$ | $\delta_H^2$ (multiplicity) | $\delta_C^1$ | $\delta_H^2$ (multiplicity) | $\delta_C^1$ | $\delta_H^2$ (multiplicity) |
| 1 | 28.29 | 2.02 (m), 1.19 (m) | 25.64 | 2.11, 1.33 | 34.34 | 1.42 (m) |
| 2 | 17.64 | 1.85 (m), 1.55 (m) | 17.52 | 1.57, 1.48 | 17.04 | 1.73, 1.4 |
| 3 | 37.65 | 1.83 (m), 1.08 (m) | 37.12 | 1.77, 1.07 | 37.74 | 1.60, 1.15 |
| 4 | 39.64 | — | 37.91 | — | 38.89 | — |
| 5 | 79.79 | — | 85.25 | — | 77.23 | — |
| 6 | 73.70 | 4.31 (bt, 2.82 Hz) | 29.67 | | 72.73 | 4.11 (bt, 3.02 Hz) |
| 7 | 38.54 | 2.37 (m), 1.6 (dd, 15.22, 2.77 Hz) | 50.97 | 1.91, 3.69 | 43.57 | 2.14, 1.78 |
| 8 | 77.21 | — | 81.01 | — | 74.65 | — |
| 9 | 78.71 | — | 78.93 | — | 49.02 | 1.72 |
| 10 | 43.23 | — | 48.40 | — | 40.12 | — |
| 11 | 23.39 | 2.29 (m), 1.43 | 23.79 | 2.29, 1.47 | 17.58 | 1.84, 1.47 |
| 12 | 31.43 | 1.78 (dd, 13.82, 3.87 Hz), 1.29 (d, 13.82 Hz) | 31.25 | 1.80, 1.38 | 37.78 | 1.59, 1.40 |
| 13 | 35.36 | — | 35.64 | — | 36.32 | — |
| 14a | 46.57 | 1.95 (d, 14.14 Hz) | 46.76a | 2.16 (m) | 51.09 | 1.43, 1.39 |
| 14b | 46.57 | 1.15 (dd, 14.14, 2.05 Hz) | 46.76b | , 1.06 (m) | | |
| 15 | 151.04 | 5.79 (dd, 10.65, 17.65) | 150.49 | 5.78 (dd, 10.82, 17.42) | 151.12 | 5.74 (dd, 11.06, 17.65) |
| 16a | 108.90 | 4.92 (dd, 17.65, 1.01 Hz) | 109.24 | 4.93 (d, 10.82) | 108.90 | 4.9 (dd, 17.65, 1.08 Hz) |
| 16b | 108.90 | 4.87 (dd, 10.65, 1.01 Hz) | 109.24 | 4.88 (d, 17.42) | 108.90 | 4.85 (dd, 11.06, 1.08 Hz) |
| 17 | 24.96 | 1.28 (s) | 25.02 | 1.26 (s) | 24.02 | 1.22 (s) |
| 18 | 27.37 | 0.99 (s) | 27.94 | 0.99 (s) | 27.66 | 1.00 (s) |
| 19 | 25.91 | 1.47 (s) | 24.54 | 1.40 (s) | 25.26 | 1.44 (s) |
| 20 | 19.68 | 1.54 (s) | 19.48 | 1.21 (s) | 18.07 | 1.42 (s) |

TABLE 2

$^1$H and $^{13}$C NMR values for compound 4 (in CDCl$_3$)

| | 4 | |
|---|---|---|
| No. | $^{13}$C (δ) | $^1$H (δ) |
| 1 | 141.64 | — |
| 2 | 143.42 | — |
| 3 | 115.67 | 6.74 |
| 4 | 133.20 | — |
| 5 | 120.98 | 6.65 (d, 8 Hz) |
| 6 | 115.32 | 6.81 (d, 8 Hz) |
| 7 | 39.47 | 3.295 (d, 6.53 Hz) |
| 8 | 137.60 | 5.95m |
| 9 | 115.56 | 5.08 |

TABLE 2-continued

¹H and ¹³C NMR values for compound 4 (in CDCl₃)

| No. | ¹³C (δ) | ¹H (δ) |
|---|---|---|
| | 4 | |
| OH | — | 5.40bs |
| OH | — | 5.40bs |

According to another embodiment, the compounds isolated are studied for various activities including for possible action against *Mycobacterium tuberulosis* and other uses, not limited to pharmacotherapeutics.

The compounds 1-4 of the invention are screened for their antimicrobial activity and found that the compound found to possess good anti-microbial activity against *M. tuberculosis* as shown in table 3. The compound 3 is screened for its anti-tumor activity and found that the activity of compound 3 is comparable to that of known standard drug, paclitaxel, as shown in Table 3.

Thus, in a preferred embodiment, the invention provides pharmaceutical compositions comprising at least one component selected from extract(s) or fraction(s) standardized to pimarane diterpenes class of compounds isolated from *A. verticillatus* for prevention, treatment, inhibition or controlling growth and proliferation of tuberculosis in mammals.

Thus, in a preferred embodiment, the invention provides pharmaceutical compositions comprising at least one component selected from extract(s) or fraction(s) standardized to pimarane diterpenes class of compounds isolated from *A. verticillatus* for prevention, treatment, inhibition or controlling growth and proliferation of variety of cancer in mammals.

The cancer may be selected from breast cancer, prostate cancer, pancreatic cancer or bladder cancer etc.

In another preferred embodiment, the invention provides pharmaceutical composition comprising at least one component selected from extract(s) or fraction(s) standardized to pimarane diterpenes class of compounds isolated from *Anisochilus verticillatus* in combination with at least one component selected from biologically active ingredient; pharmaceutically or dietetically acceptable active ingredients, vitamins, amino acids, minerals together with pharmaceutically or dietetically acceptable excipients, vehicles, carriers and diluents or mixtures thereof, for prevention, treatment, inhibition or controlling growth and proliferation of tubercular activity in mammals.

In yet another preferred embodiment, the invention provides pharmaceutical composition comprising at least one component selected from extract(s) or fraction(s) standardized to pimarane diterpenes class of compounds isolated from *A. verticillatus* in combination with at least one component selected from biologically active ingredient; pharmaceutically or dietetically acceptable active ingredients, vitamins, amino acids, minerals together with pharmaceutically or dietetically acceptable excipients, vehicles, carriers and diluents or mixtures thereof, for prevention, treatment, inhibition or controlling growth and proliferation of cancers in mammals.

The pharmaceutically or dietetically acceptable excipients encompasses vehicles, diluents and carriers such as surfactants, binders, disintegrators, lubricants, preservatives, stabilizers, buffers etc known in the art. The composition of the invention may be formulated into conventional dosage form such as tablets, granules, soft capsule, hard capsule, pellets, soft gel capsules, pills, powders, emulsions, suspensions, syrups, aerosols, food, beverages, injections, and suppositories.

In yet another embodiment, the invention also provides the method of treating or controlling the proliferation of tuberculosis in mammals comprising administering extracts and fractions standardized to pimarane diterpenes class of compounds isolated from *A. verticillatus* or their pharmaceutical composition(s).

In another embodiment, the invention provides use of extracts and fractions standardized to pimarane diterpenes class of compounds isolated from *A. verticillatus* or their composition(s) in preparation of medicament useful for treating or controlling the proliferation of tuberculosis in a subject.

In another embodiment, the invention provides use of extracts and fractions standardized to pimarane diterpenes class of compounds isolated from *A. verticillatus* or their composition(s) in preparation of medicament useful for treating or controlling the proliferation of cancer in a subject. The subject according to the invention is a mammal.

In another embodiment, the invention provides *A. verticillatus* derived extracts and fractions wherein the concentration of the extracts and fractions in an amount of 0.01% to 99% by weight to impart the desired therapeutic effect and the rest being an excipient or any additional active agent that may bring synergy for this composition.

The composition(s) according to the invention are administered orally, topically, parenterally or by inhalation to a subject or mammal or warm blooded animal in need thereof, wherein said ingredient or composition(s) are administered once a day or multiple administrations per day or as prescribed by physician/doctor.

The following examples, which include preferred embodiments, will serve to illustrate the practice of this invention, it being understood that the particulars shown are by way of example and for purpose of illustrative discussion of preferred embodiments of the invention.

EXAMPLES

Example 1

Powdered aerial parts of *Anisochilus verticillatus* (1.13 kg) were extracted with acetone (3×3 L, 14 h) at 25° C. temperature. The mixture was filtered and concentrated under reduced pressure to provide a greenish acetone extract (39.7 g). Acetone extract, 38 g, was fractionated by column chromatography (CC) with increasing polarity of acetone from 5 to 50% in petroleum ether to give 18 fractions (AV1-AV18).

Fraction AV4 (1.8 g) was subjected to CC with acetonitrile from 1% to 4% in chloroform to give 13 sub-fractions (AV4a-AV4m). Fractions AV4i, AV4j and AV3h were combined and subjected to CC in 3% acetonitrile in chloroform to give mixture of compounds 1 and 2 which was separated and purified by preparative TLC in 30% ethyl acetate in cyclohexane. From fractions AV4k, AV4l and AV4m, compound 3 was crystallized out.

Fraction AV5 (4.0 g) was subjected to CC with acetonitrile from 1% to 15% in chloroform to give 15 sub-fractions (AV5a-o). Sub fractions AV5n and AV5o contained compound 4, which was purified by preparative TLC in 10% ethyl acetate in benzene.

Example 2

Anti-Mycobacterial Activity

All the isolated compounds and whole acetone extract were tested for their in vitro effect against *Mycobacterium tuberculosis* H37Ra culture maintained in-house.

*M. tuberculosis*, H37Ra (ATCC 25177) cells were grown to logarithmic phase (O.D.595~1.0) in a defined medium (M. pheli medium) under aerobic conditions in a shaker incubator (Thermo Electron Corporation Model 481) maintained at 150 rpm and 37° C. After growth, the culture was sonicated for 2 min using a water bath sonicator. Sonicated cells were used for inoculation in micro plate wells. 250 μl of the culture containing ~10 5 cells/ml was added to each well of 96 well plates. 2.5 μl of the test samples dissolved in DMSO was added to the wells to attain a final concentration of 100 ug/ml respectively for the preliminary screening. Dose response curve of the active compounds was carried out by making serial dilutions of the test samples. Then, the plate was incubated in a CO2 incubator at 37° C. The plate was taken out on the 8th day of incubation to measure the viable cell counts. The optical density of the culture was measured before addition of XTT at 470 nm which was served as a blank for the MIC calculations. 200 μM XTT was added and incubated for 20 min at 37° C. after shaking for 1 min. After 20 min of incubation, 60 μM menadione was added and incubated at 37° C. for 40 min after mixing of 1 min. Finally, the optical density of the suspension was measured at 470 nm by using microplate reader.

Compounds 1-4 showed inhibition of *M. tuberculosis* (Table 3).

Example 3

Cytotoxicity Studies

Compounds 3 was tested at IC90 values and also at higher concentration, 100 μg/ml, for their in vitro cytotoxicity against THP-1 (Human acute leukemia cells) cell lines procured from National Cell Repository, India. The percent inhibition values are given in Table 3.

About 10,000 cells were taken per well in 96-well tissue culture plates and treated with compound 3 at IC90 values and also at higher concentration, 100 μg/ml for 72 h. Vehicle control (DMSO, 1%) and positive control (Paclitaxel, 100 μg/ml) were run simultaneously. Cell proliferation was assessed with 10 μl from 5 mg/ml stock solution of tetrazolium salt (MTT) dissolved in cell culture medium and subsequently incubated for additional 1 h at 37° C., 5% of CO2 and 95% humidity in incubator. The violet coloured formazan crystals formed were solubilized in 200 μl of isopropanol and incubated for another 4 h. The optical density was read on a micro plate reader (Spectramax plus384 plate reader, Molecular Devices Inc) at 490 nm filter against a blank prepared from cell-free wells. Absorbance given by cells treated with the carrier DMSO alone was taken as 100% cell growth. All experiments were performed in triplicate, and the quantitative value was expressed as the average±standard deviation.

Compound 3 at 100 μg/ml showed 57.23% inhibition of Thp-1 cell line (Table 3).

TABLE 3

Effect of 1, 2, 3 and 4 on the viability of Thp-1 cell line and *M. tuberculosis* bacilli.

| Compound | % Inhibition on Thp-1 cell line at 100 μg/ml | $IC_{90}$[b] value determined against *M. tuberculosis* (μg/ml) |
|---|---|---|
| 1 | Not tested | 42.92[c] |
| 2 | Not tested | 20.00 |
| 3 | 57.23 | 35.03[c] |
| 4 | Not tested | 12.50[d] |
| Isoniazid | — | 0.05 ± 0.003 |
| Paclitaxel | 61% ± 0.501 | — |
| Vehicle Control[a] | No inhibition | No inhibition |

[a]1% Dimethyl sulfoxide (DMSO),
[b]Concentration of compounds exhibiting 90% inhibition against growth of *M. tuberculosis*.
[c]% inhibition at 100 μg/ml
[d]$IC_{50}$ = Concentration of compounds exhibiting 50% inhibition against growth of *M. tuberculosis*.

From the above Table it is evident that the compound 3 possess anti-cancer activity and compounds 1-4 possess antimycobacterial activity.

Example 4

Compositions Derived from *Anisochilus verticillatus*

Example (i)

Composition

| | |
|---|---|
| Compound 1 | 10.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Mix active ingredient and Magnesium stearate and may be filled in a capsule of suitable size.

Mode of administration: The capsule may be had with water of juice

Example (iv)

Composition

| | |
|---|---|
| Compound of Formula I | 20.0% w/w |
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.

Evaporate water to adsorb color and flavor on mannitol.

Mix active ingredient and Magnesium stearate and may be filled in a capsule of suitable size.

Mode of Administration;
Mode of administration: The capsule may be had with water of juice Example (v)

Composition

| Compound of Formula I | 10.0% w/w |
|---|---|
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.
Evaporate water to adsorb color and flavor on mannitol.
Mix active ingredient and Magnesium stearate and may be compressed as tablet.
Mode of Administration;
Mode of administration: The tablet may be had with water of juice Example (vi)

Composition

| Compound of Formula I | 10.0% w/w |
|---|---|
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.
Evaporate water to adsorb color and flavor on mannitol.
Mix active ingredient and Magnesium stearate and may be compressed as tablet.
Mode of administration: The tablet may be had with water of juice Example (vii)

Composition

| Compound of Formula I | 5.0% w/w |
|---|---|
| Color Amaranth | 0.3% w/w |
| Raspberry Flavor | 0.7% w/w |
| Magnesium stearate | 2.0% w/w |
| Mannitol | q.s. to 100.0% w/w |

Procedure: Dissolve mannitol in water, add color and flavor to it.
Evaporate water to adsorb color and flavor on mannitol.
Mix active ingredient and Magnesium stearate and fill in pouch or bottle.
Mode of Administration:
Disperse the powder in water/juice.

ADVANTAGES OF PRESENT INVENTION

After assaying the compounds 1, 2, 3, and 4 of the present invention, these compounds are found to be effective against *Mycobacterium tuberculosis* due to their anti-tubercular property.

Compound 3 showed anti-cancer activity against THP-1 cell lines.
The plant of the present investigation is exhibits both anti-TB and ant-cancer activities and hence holds a promising for being used in the treatment of tuberculosis and cancer.

We claim:
1. A compound of general formula I

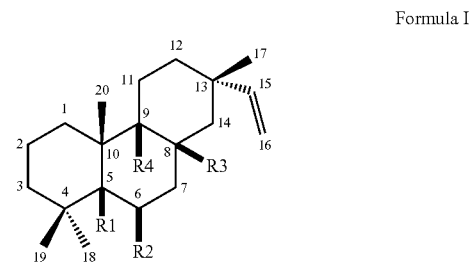

Formula I wherein R1, R2, R3 and R4 could be either α or β oriented; R1 and R3 are —OH or the substituents R1 and R3 together form peroxide (—O—O—) linkage; R2 and R4 are independently selected from the group consisting of H and OH.

2. The compound as claimed in claim 1, wherein said compound is represented by a group of the following compounds

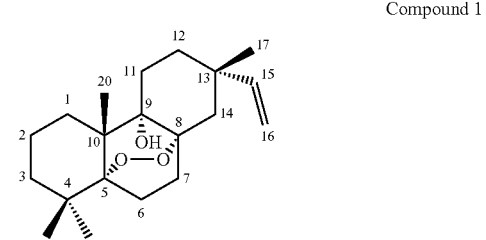

Compound 1

(2S,4aS,4bR,8aR,10aS)-2,4b,8,8-tetramethyl-2-vinyldodecahydro-8a,10a-epidioxyphenanthren-4a-ol wherein, the substituents R1 and R3 together form peroxide (—O—O—) linkage;
R2 is hydrogen and R4 is OH; and wherein the substituents R1 to R4 are α oriented

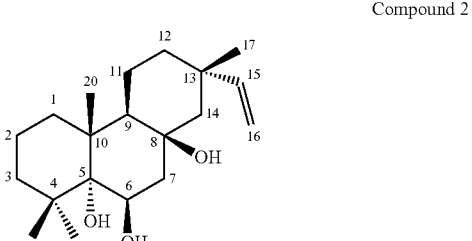

Compound 2

(2S,4aR,4bR,8aR,9R,10aS)-2,4b,8,8-tetramethyl-2-vinyltetradecahydrophenanthrene-8a,9,10a-triol wherein, R1, R2 and R3 are OH" and R4 is H; and wherein the substituents R1 and R2 are trans while R2 and R4 are also trans;

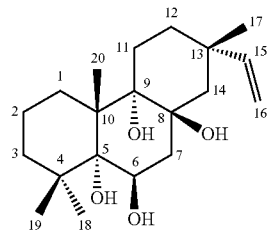

Compound 3

(2S,4aS,4bS,8aR,9R,10aS)-2,4b,8,8-tetramethyl-2-vinyltetradecahydrophenanthrene-4a,8a,9,10a-triol wherein, R1, R2, R3 and R4 are OH; and wherein the substituents R1 and R2 are trans while R2 and R4 are also trans.

3. The compound as claimed in claim 1, wherein said compound is isolated from *Anisochilus verticillatus*.

4. The compound as claimed in claim 1, wherein said compound is useful for prevention, treatment, inhibition or controlling growth and proliferation of tubercular activity in mammals and for treatment, inhibition or controlling growth and proliferation of leukemia.

5. The compound as claimed in claim 1, wherein said compound is useful for treating or controlling proliferation of tuberculosis in a mammal.

6. The compound as claimed in claim 1, wherein % inhibition on Thp-1 cell line of compound 3 is 57.23 at 100 μg/ml.

7. The compound of general formula I as claimed in claim 1, wherein the $IC_{90}$ value of compounds of general formula I against *M. tuberculosis* is in the range of 12.5 to 42.92 μg/ml.

8. A process for the extraction of a compound of general formula I as claimed in claim 1, wherein the process comprises the steps of:

i) pulverizing aerial parts of *A. verticillatus* followed by extraction with acetone at room temperature in the range of 25 to 30° C., filtering acetone solubles and concentrating under reduced pressure in the range of 50-100 mm Hg to obtain a greenish acetone extract, ii) separating the extract as obtained in step i) by using column chromatography (CC) with increasing polarity of the polar solvent using a gradient of acetone from 5% to 50% in pet ether to obtain 18 fractions (AV1-AV18), iii) subjecting fraction AV3 of step ii) to CC with a gradient of acetonitrile from 0.5% to 3% in chloroform to collect 8 fractions (AV3a-h), iv) subjecting fraction AV4 of step ii) to CC using gradient of acetonitrile from 1% to 4% in chloroform to collect 13 fractions (AV4a-m), combining fractions AV4i and AV4j of step iv) and AV3h of step iii) and subjecting them to CC with 3% acetonitrile in chloroform to obtain a mixture of compounds 1 and 2 and separating and purifying by preparative TLC using 20% acetone in cyclohexane as the developing system, vi) crystallizing from fractions AV4k, AV4l and AV4m of step iv) to obtain compound 3, vii) subjecting fraction AV5 of step ii) to CC using elution gradient acetonitrile from 1% to 15% in chloroform to collect 15 fractions (AV5a-o), viii) subjecting fractions AV5n and AV5o of step vii) to preparative TLC using developing system 10% ethyl acetate in benzene to isolate compound 4.

9. A pharmaceutical composition comprising at least one compound selected from pimarane diterpenes class of compounds of general formula I as claimed in claim 1 for prevention, treatment, inhibition or controlling growth and proliferation of tuberculosis in mammals.

10. A pharmaceutical composition comprising at least one compound selected from pimarane diterpenes class of compounds of general formula I as claimed in claim 1 for for treatment, inhibition or controlling growth and proliferation of leukemia in mammals.

\* \* \* \* \*